United States Patent [19]

Kubota et al.

[11] Patent Number: 5,559,083

[45] Date of Patent: Sep. 24, 1996

[54] COMPOSITION COMPRISING AN ISOTHIAZOLONE COMPOUND

[75] Inventors: Naoki Kubota, Ibaraki; Taiki Kusaka, Amagasaki, both of Japan

[73] Assignee: Takeda Chemical Industries, Ltd., Osaka, Japan

[21] Appl. No.: 415,517

[22] Filed: Apr. 3, 1995

[30] Foreign Application Priority Data

Apr. 4, 1994 [JP] Japan ................... 6-066281

[51] Int. Cl.$^6$ ............ A01N 43/80; C07D 275/02; C07D 275/04
[52] U.S. Cl. ............ 504/269; 548/209; 548/213; 514/372
[58] Field of Search ............... 548/213, 209; 504/269; 514/372

[56] References Cited

U.S. PATENT DOCUMENTS

| | | | |
|---|---|---|---|
| 5,024,997 | 6/1991 | Motola et al. | 514/58 |
| 5,306,725 | 4/1994 | Sano et al. | 514/372 |
| 5,376,509 | 12/1994 | Yoshimoto et al. | 430/449 |

FOREIGN PATENT DOCUMENTS 5-247011  9/1993  Japan.

*Primary Examiner*—Johann Richter
*Assistant Examiner*—Laura L. Stockton
*Attorney, Agent, or Firm*—Wenderoth, Lind & Ponack

[57] ABSTRACT

A composition comprising an isothiazolone compound mixed with a branched cyclodextrine, wherein the isothiazolone compound can be stabilized to water, so that it is possible to provide an aqueous solution comprising an isothiazolone compound which is excellent in storage stability and aqueous solution stability.

12 Claims, No Drawings

COMPOSITION COMPRISING AN ISOTHIAZOLONE COMPOUND

BACKGROUND OF THE INVENTION

1. Field of the Invention

The present invention relates to a composition comprising an isothiazolone compound mixed with a branched cyclodextrine, which is stable to water.

2. Description of the Prior Art

With increasing demand for industrial water, use of recycle water system has been extensively carried on, but in such use, restraint and control of proliferation of microbe are becoming important problems. And with diversification of industrial materials besides such industrial water, damage caused by proliferation of microbe and that by growth of mold cover a wide range. Especially, it is of urgent necessity to deal with a slime problem of fungi, bacteria, yeasts, algae, etc. which are parasitic on drainage used in a process of paper manufacturing, industrial cooling water, lubricating oil for metal processing, aqueous emulsion, or paper, timber, plywood, paste, pulp, fiber, etc., or microbe damage and so on.

Recently, isothiazolone compounds have been given attention as industrial biocides for the purpose of preventing microbe from generating or removing it, and being found that they have a wide range of application and excellent effects.

Generally speaking, it is desirable for industrial biocides of this kind to be solutions, but it has been known that these isothiazolone compounds are easily decomposed by reducing nucleophilic bodies and so on. Therefore, they are very unstable and have remarkable quality changes for aqueous solution preparations, while an increased proportion of an organic solvent in the solution component brings about, for example, a problem on storage with regard to the Fire Service Act, leading to the difficulty in providing stable products as solutions.

Then, aqueous solution preparations containing an isothiazolone compound which are stable as products for a long period are required. For example, in Japanese Patent Laid-Open Publication Nos. 78102/84, 78103/84, 78104/84, 78109/84, 35603/88 and 50322/88, it was proposed to stabilize an isothiazolone compound in an aqueous solution with metal salt (MXn: M is a metal selected from among magnesium, calcium, potassium, copper, iron, zinc, manganese, silver, cobalt, nickel and so on, X is an anion selected from among chloride, bromide, iodide, sulfate, nitrate, nitrite, acetate, perchlorate, bisulfate, bicarbonate, oxalate, carbonate, phosphate and so on, n is an integer to be fitted for the valence of anion and cation) in order to stabilize an aqueous solution preparation. However, metal salt containing metal ions such as calcium and magnesium is not desirable since it causes the occurrence of turbidity or precipitate in the subject. Especially in the case that it is added to anionic macromolecular disperse system, co-existing metal stabilizers make the anionic macromolecular disperse system unstable, resulting in the occurrence of cohesion, a fatal problem, so that the aqueous solution preparations disclosed in the above publications are not sufficiently desirable as products. And conventional metal salt besides the above does not have a stabilization effect sufficient as a stabilizer or have the same defect as magnesium salt and so on, so that it also cannot provide a desirable product. Besides, alkali salt of iodic acid or that of bromic acid were proposed in Japanese Patent Laid-Open Publication No. 286815/93, but it is very difficult to use these stabilizers, since these belong to class 1 dangerous goods and have a danger of explosion. A composition whose skin stimulativity and mucous membrane stimulativity were remarkably reduced by making a clathrate compound with addition of α, β and γ cyclodextrine was proposed in Japanese Patent Laid-Open Publication No. 247011/93, but it has been used only as a dust or suspension.

SUMMARY OF THE INVENTION

In order to solve these problems, the present inventors had earnestly studied and found that it is possible to stabilize an isothiazolone compound to water by mixing a branched cyclodextrine, completing the present invention. That is, the present invention relates to a composition comprising an isothiazolone compound mixed with a branched cyclodextrine, which is stable to water, and to providing an aqueous preparation comprising an isothiazolone compound which is excellent in storage stability and aqueous solution stability.

The compositions comprising an isothiazolone compound in the present invention show stable effects for a long period of time, and can be used as slime controllers, biocides and biocidal cleaning agents in paper manufacturing pulp factories and a process of cooling water circulation, or industrial biocides such as antiseptics of metal processing oil, textile oils, casein, starch, coating color, paint, emulsion, latex and sizings.

DETAILED DESCRIPTION OF THE INVENTION

An isothiazolone compound in the present invention is represented by the following formula (1)

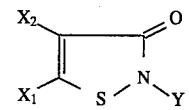

wherein Y is a hydrogen atom or an optionally substituted hydrocarbon group, and $X_1$ and $X_2$ are each independently, a hydrogen atom, a halogen atom, a lower alkyl or $X_1$ and $X_2$ taken together to form a benzene ring which may be optionally substituted.

In the isothiazolone compound represented by the above formula (1), Y is a hydrogen atom or an optionally substituted hydrocarbon group. As a hydrocarbon group represented by Y, alkyl, alkenyl, alkynyl, cycloalkyl, aryl, etc., preferably alkyl and cycloalkyl, etc., more preferably alkyl, etc., are exemplified.

As alkyl represented by Y, alkyl having 1 to 10 carbon atoms such as methyl, ethyl, propyl, isopropyl, butyl, isobutyl, sec-butyl, tert-butyl, pentyl, hexyl, heptyl, octyl, isooctyl, sec-octyl, tert-octyl, nonyl and decyl, preferably alkyl having 1 to 3 carbon atoms such as methyl and ethyl, and alkyl having 7 to 9 carbon atoms such as octyl and tert-octyl, more preferably alkyl having 1 to 3 carbon atoms such as methyl and ethyl, are exemplified.

As alkenyl represented by Y, alkenyl having 2 to 6 carbon atoms such as vinyl, allyl, isopropenyl. 1-propenyl, 2-propenyl and 2-methyl-1-propenyl, preferably alkenyl having 2 to 4 carbon atoms such as vinyl and allyl, are exemplified.

As alkynyl represented by Y, alkynyl having 2 to 6 carbon atoms such as ethynyl, 1-propynyl, 2-propynyl, butynyl and pentynyl, preferably alkynyl having 2 to 4 carbon atoms such as ethynyl and propynyl, are exemplified.

As cycloalkyl represented by Y, cycloalkyl having 3 to 10 carbon atoms such as cyclopropyl, cyclobutyl, cyclopentyl, cyclohexyl, cycloheptyl and cyclooctyl, preferably cycloalkyl having 5 to 7 carbon atoms such as cyclopentyl and cyclohexyl, are exemplified.

As aryl represented by Y, aryl having 6 to 14 carbon atoms such as phenyl, naphthyl, anthryl and phenanthryl, preferably aryl having 6 to 10 carbon atoms such as phenyl, are exemplified.

As substituents of an optionally substituted hydrocarbon group represented by Y, hydroxyl, a halogen atom (e.g. chlorine, fluorine, bromine and iodine), cyano, amino, carboxyl, alkoxy (e.g. alkoxy having 1 to 4 carbon atoms such as methoxy and ethoxy), aryloxy (e.g. $C_{6-10}$ aryloxy such as phenoxy), alkylthio (e.g. alkylthio having 1 to 4 carbon atoms such as methylthio and ethylthio) and arylthio (e.g. $C_{6-10}$ arylthio such as phenylthio), preferably a halogen atom, $C_{1-4}$ alkoxy, etc., are exemplified. The hydrocarbon group may be optionally substituted by one to five, preferably one to three, of these substituents, which may be either identical to or different from each other. And examples of Y are preferably methyl, octyl and so on, more preferably methyl and so on.

In an isothiazolone compound represented by the above formula (1), $X_1$ and $X_2$ are each independently, a hydrogen atom, a halogen atom, a lower alkyl or $X_1$ and $X_2$ taken together to form a benzene ring which may be optionally substituted.

As a halogen atom represented by $X_1$ and $X_2$, fluorine, chlorine, bromine, iodine and so on, preferably chlorine, etc., are exemplified.

As alkyl represented by $X_1$ and $X_2$, alkyl having 1 to 6 carbon atoms such as methyl, ethyl, propyl, isopropyl, butyl, isobutyl, sec-butyl, tert-butyl and pentyl, preferably alkyl having 1 to 4 carbon atoms such as methyl, ethyl and propyl, are exemplified. And examples of $X_1$ are preferably a hydrogen atom or chlorine, etc., more preferably chlorine, etc., and examples of $X_2$ are preferably a hydrogen atom or chlorine, etc., more preferably a hydrogen atom, etc.

As substituents of a benzene ring, hydroxyl, a halogen atom (e.g. chlorine, fluorine, bromine and iodine), cyano, amino, carboxyl, alkyl (e.g. alkyl having 1 to 4 carbon atoms such as methyl, ethyl and propyl), alkoxy (e.g. alkoxy having 1 to 4 carbon atoms such as methoxy and ethoxy) and so on, preferably a halogen atom, $C_{1-4}$ alkyl, etc., are exemplified. The benzene ring may be optionally substituted by one to four, preferably one to two, of these substituents, which may be either identical to or different from each other.

As examples of the isothiazolone compound (1), 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 2-ethyl-4-isothiazoline-3-one, 4,5-dichloro-2-cyclohexyl-4 -isothiazoline-3-one, 5-chloro-2-ethyl-4 -isothiazoline-3-one, 5-chloro-2-t-octyl-4 -isothiazoline-3-one, 1,2 -benzisothiazoline-3-one and so on, preferably 5 -chloro-2-methyl-4-isothiazoline-3-one, 2 -methyl-4-isothiazoline- 3-one, 2-n-octyl-4-isothiazoline-3-one, 4,5-dichloro-2 -n-octyl-4-isothiazoline-3-one, 1,2-benzisothiazoline- 3-one, etc., more preferably 5-chloro-2-methyl-4 -isothiazoline-3-one, 2-n-octyl-4-isothiazoline- 3-one, 4,5-dichloro-2-n-octyl-4-isothiazoline-3-one, 1,2 -benzisothiazoline-3-one, etc. are exemplified. These compounds can be properly mixed to be used.

These isothiazolone compounds can be produced by the methods described in U.S. Pat. Nos. 3,761,488, 3,849,430, 3,870,795, 4,067,878, 4,150,026, 4,241,214, 3,517,022, 3,065,123, 3,761,489, 3,849,430, etc. or their equivalents.

As a branched cyclodextrine used in the present invention, a cyclodextrine ring with an attached monosaccharide or disaccharide branch such as glucose or maltose, that is, glucosylcyclodextrine such as G1-β-cyclodextrine and G1-γ-cyclodextrine, which is a cyclodextrine ring with an attached glucose, maltosylcyclodextrine such as G2-α-cyclodextrine, G2-β-cyclodextrine and G2-γ-cyclodextrine, which is a cyclodextrine ring with an attached maltose, G1-G1-, G1 -G2-, or G2-G2-maltotoriosylcyclodextrine, which is a cyclodextrine ring with an attached maltotoriose such as G3-α-cyclodextrine, G3-β-cyclodextrine and G3-γ-cyclodextrine, wherein a maltotriosyl is attached to a cyclodextrine ring at the 2- or higher positions, and so on, are cited. Preferably glycosylcyclodextrine and maltosylcyclodextrine are exemplified.

It is desired that a composition comprising an isothiazolone compound in the present invention is a solution, and contains water. From the viewpoint of the solubility of an isothiazolone compound, it may further contain an organic solvent. As the organic solvent, alcoholic solvents such as methyl alcohol, ethyl alcohol, propyl alcohol, isopropyl alcohol and butyl alcohol, ketone solvents such as acetone, methyl ethyl ketone and methyl isobutyl ketone, hydrocarbon halide solvents such as dichloroethane, chloroform and carbon tetrachloride, ether solvents such as dioxane and tetrahydrofuran, polar solvents such as dimethylformamide, dimethylsulfoxide and acetonitrile, and glycol solvents such as ethylene glycol, diethylene glycol, polyethylene glycol, propylene glycol, dipropylene glycol, tripropylene glycol, polypropylene glycol, 1,4-butanediol, 1,5 -pentanediol, ethylene glycol monomethyl ether, ethylene glycol monoethyl ether, ethylene glycol monobutyl ether, diethylene glycol monomethyl ether, diethylene glycol monoethyl ether and tripropylene glycol monomethyl ether, are exemplified. Preferably glycol solvents, especially ethylene glycol, diethylene glycol, propylene glycol, dipropylene glycol, ethylene glycol monomethyl ether, ethylene glycol monoethyl ether, diethylene glycol monomethyl ether and diethylene glycol monoethyl ether, are exemplified.

A composition comprising an isothiazolone compound in the present invention consists of 0.1–10 wt % of isothiazolone compound mixed with 0.1–99.1 wt % of a branched cyclodextrine. In the case of adding water, water is added in the range of 1–100 wt % to the composition comprising an isothiazolone compound of 10 wt %. In the case of further adding an organic solvent, an organic solvent is added in the range of 1–100 wt % to the composition comprising an isothiazolone compound of 10 wt %. The proportion of a branched cyclodextrine depends on preparation, but in the case of an aqueous preparation having a high water content, for example, it is better to increase the proportion of a branched cyclodextrine.

In the preparation of a solution, an isothiazolone compound is made by stirring and mixing every component of the prescribed quantity using industrial original bodies on the market such as Kathon WT, Kathon LX plus (produced by Rohm and Haas Company), Zonen C and Zonen F (produced by Ichikawa Gohsei Chemical Company, Ltd.) with a stirrer until it becomes completely uniformity. Especially, an isothiazolone compound and a branched cyclodextrine are prepared to be finally 0.1–40 wt %, preferably 1–20 wt %, and 0.1–60 wt %, preferably 5–40 wt %, respectively.

Furthermore, in the present invention, additives whose purpose, usage and so on have been well-known, such as surfactants and oxidation inhibitors, can be added.

As the surfactants, well-known surfactants such as soaps, nonionic surfactants, anionic surfactants, cationic surfactants, amphoteric surfactants and high molecular surfactants can be used. Among them, nonionic surfactants and anionic surfactants are preferably used.

As the nonionic surfactants, polyoxyalkylene aryl phenyl ether, polyoxyethylene nonyl phenyl ether, ethylene oxide-propylene oxide block-copolymer and so on are exemplified.

As the anionic surfactants, alkylbenzene sulfonic acid metal salt, alkylnaphthalene sulfonic acid metal salt, polycarboxylic acid surfactants, dialkyl sulfosuccinic ester metal salt, polyoxyethylene distyrenyl phenyl ether sulfate ammonium salt, lignin sulfonic acid metal salt, etc. are cited, and as metal salt, sodium salt, potassium salt, magnesium salt, etc. are exemplified.

As the oxidation inhibitors, phenol oxidation inhibitors such as 2,6-di-t-butyl-4-methylphenol and 2,2'-methylenebis [4-methyl-6-t-butylphenol], amine oxidation inhibitors such as alkyldiphenylamine and N,N'-di-s-butyl-p-phenylenediamine and so on, are exemplified.

When the composition is a solution, for example, these surfactants and oxidation inhibitors are added in the ratio of 0.1–5 wt % to a solution of 100 wt %.

DESCRIPTION OF PREFERRED EMBODIMENTS

The present invention is concretely described below with examples and comparative examples, but is not limited to the examples. Here, the terms used in the examples and comparative examples are as follows:

Zonen F (an industrial original body containing ca. 10 wt % of 5-chloro-2-methyl-4-isothiazoline-3-one produced by Ichikawa Gohsei Chemical Company, Ltd.)

Kathon LX Plus Concentrate (an industrial original body containing 5-chloro-2-methyl-4-isothiazoline-3-one of about 18 wt % produced by Rohm and Haas Company)

a branched cyclodextrine (30% of an aqueous solution: Isoeleat L, produced by Nikken Chemical Ltd., containing 50 wt % or more of maltosylcyclodextrine): a branched CD, and ethylene glycol: EG.

EXAMPLE 1

One hundred grams of a solution was obtained by previously mixing 30 g of Zonen F with 11 g of EG, while previously mixing 29 g of Isoeleat L (a 20 g of branched CD and 9 g of water) with 30 g of water, and then mixing both of them.

EXAMPLES 2–8

Each solution in Examples 2–8 was obtained by mixing and regulating every material to result in the composition (wt %) shown in Table 1 in the same manner as that in Example 1.

TABLE 1

| Examples | 2 | 3 | 4 | 5 | 6 | 7 | 8 |
|---|---|---|---|---|---|---|---|
| Zonen F | 30 | 30 | 30 | 30 | 30 | 30 | 30 |
| Branched CD | 30 | 30 | 30 | 30 | 35 | 35 | 35 |
| Water | 10 | 20 | 30 | 40 | 15 | 25 | 35 |
| EG | 30 | 20 | 10 | 0 | 20 | 10 | 0 |

COMPARATIVE EXAMPLE 1

One hundred grams of a solution was obtained by dissolving 30 g of Zonen F in 50 g of EG and adding 20 g of water thereto.

COMPARATIVE EXAMPLES 2–7

Each solution in Comparative Examples 2–7 was obtained by mixing and regulating every material to result in the composition (wt %) shown in Table 2 in the same manner as that in Comparative Example 1.

TABLE 2

| Comparative Examples | 2 | 3 | 4 | 5 | 6 | 7 |
|---|---|---|---|---|---|---|
| Zonen F | 30 | 30 | 30 | 30 | 30 | 30 |
| Water | 20 | 30 | 40 | 15 | 25 | 35 |
| EG | 50 | 40 | 30 | 55 | 45 | 35 |

EXPERIMENTAL EXAMPLE 1

The solutions according to Examples 1–8 and Comparative Examples 1–7 were enclosed in glass containers and put in of 60° C. of the thermostat, and 7 days later, their residual rates of Cl-MIT (wt %) were measured by high-pressure liquid chromatography.

The results are shown in Tables 3 and 4.

TABLE 3

| Examples | 1 | 2 | 3 | 4 | 5 | 6 | 7 | 8 |
|---|---|---|---|---|---|---|---|---|
| Content | 88 | 97 | 90 | 87 | 84 | 86 | 84 | 86 |

TABLE 4

| Comparative Examples | 1 | 2 | 3 | 4 | 5 | 6 | 7 |
|---|---|---|---|---|---|---|---|
| Content | 0 | 0 | 0 | 0 | 0 | 0 | 0 |

It is proved that the residual rates in the solutions containing a branched cyclodextrine are higher.

EXAMPLE 9

One hundred grams of a solution was obtained by mixing 20 g of Kathon LX Plus Concentrate with 51 g of water, and further adding 29 g of Isoeleat L (20 g of a branched CD and 9 g of water) thereto to be dissolved.

EXAMPLE 10

The solution in the Example 10 having the composition shown below in Table 5 was obtained in the same manner as that in Example 9.

TABLE 5

| Examples | 9 | 10 |
|---|---|---|
| Kathon LX Plus Concentrate | 20 | 20 |
| Branched CD | 20 | 30 |
| Water | 60 | 50 |

COMPARATIVE EXAMPLE 8

One hundred grams of a solution was obtained by dissolving 20 g of Kathon LX Plus Concentrate in 80 g of water.

EXPERIMENTAL EXAMPLE 2

The solutions according to Examples 9 and 10, and Comparative Example 8 were enclosed in glass containers and put in 60° C. of the thermostat, and 7 days later, their residual rates of Cl-MIT (wt %) were measured by high-pressure liquid chromatography.

TABLE 6

| Examples | 9 | 10 |
|---|---|---|
| Content | 81 | 88 |
| Comparative Example Content | 8 | 0 |

It is proved that the residual rates in the solutions containing a branched cyclodextrine are higher.

EXAMPLE 11

One hundred grams of a solution was obtained by previously mixing 15 g of Kathon LX Plus Concentrate, 29 g of Isoeleat L (20 g of a branched CD and 9 g of water) and 11 g of water, while previously mixing 5 g of 1,2-benzisothiazoline-3-one (BIT) with 40 g of dipropylene glycol, and then mixing both of them.

COMPARATIVE EXAMPLE 9

One hundred grams of a solution was obtained by previously mixing 15 g of Kathon LX Plus Concentrate with 20 g of water, while previously mixing 5 g of 1,2-benzisothiazoline-3-one (BIT) with 60 g of dipropylene glycol, and then mixing both of them.

EXPERIMENTAL EXAMPLE 3

The solutions according to Example 11 and Comparative Example 9 were enclosed in glass containers and put in 60° C. of the thermostat, and 7 days later, their residual rates of Cl-MIT and BIT (wt %) were measured by high-pressure liquid chromatography.

TABLE 7

|  | Example 11 | Comparative Example 9 |
|---|---|---|
| Cl-MIT | 90 | 0 |
| BIT | 98 | 97 |

It is proved that the residual rate in the solution containing a branched cyclodextrine is unexceptionally higher.

What is claimed is:

1. An industrial biocide composition which consists essentially of an isothiazolone compound mixed with a branched cyclodextrin, wherein the isothiazolone compound is represented by the following formula:

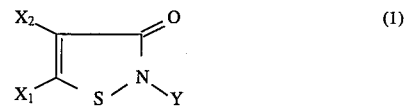

(1)

wherein Y is a hydrogen atom or an optionally substituted hydrocarbon group, and $X_1$ and $X_2$ are each independently a hydrogen atom, a halogen atom, a lower alkyl or $X_1$ and $X_2$ are taken together to form a benzene ring which may be optionally substituted.

2. The composition as claimed in claim 1, which consists essentially of a branched cyclodextrin adduct of the isothiazolone compound.

3. The composition as claimed in claim 1, wherein the branched cyclodextrin is maltosylcyclodextrin.

4. The composition as claimed in claim 1, wherein the hydrocarbon group is (i) $C_{1-10}$ alkyl, (ii) $C_{2-6}$ alkenyl, (iii) $C_{2-6}$ alkynyl, (iv) $C_{3-10}$ cycloalkyl, or (v) $C_{6-14}$ aryl, each of which may be optionally substituted by one to five substituents selected from hydroxyl, a halogen atom, cyano, amino, carboxyl, $C_{1-4}$ alkoxy, $C_{6-10}$ aryloxy, $C_{1-4}$ alkylthio and $C_{6-10}$ arylthio.

5. The composition as claimed in claim 1, wherein the lower alkyl has one to six carbon atoms.

6. The composition as claimed in claim 1, wherein the benzene ring may be optionally substituted by one to four substituents selected from hydroxyl, a halogen atom, cyano, amino, carboxyl, $C_{1-4}$ alkyl and $C_{1-4}$ alkoxy.

7. The composition as claimed in claim 1, wherein the isothiazolone compound is 5-chloro-2-methyl-4-isothiazoline-3-one.

8. The composition as claimed in claim 1, which is a solution.

9. The composition as claimed in claim 1, which further contains water.

10. The composition as claimed in claim 1, which further contains an organic solvent.

11. The composition as claimed in claim 10, wherein the organic solvent is a glycol solvent.

12. The composition as claimed in claim 1, wherein the branched cyclodextrin and the isothiazolone compound are premixed.

* * * * *